(12) United States Patent
Kawashima et al.

(10) Patent No.: US 7,585,989 B2
(45) Date of Patent: Sep. 8, 2009

(54) PRODUCTION PROCESS FOR CARBOXYLIC AMIDE AND DERIVATIVES THEREOF

(75) Inventors: Akiko Kawashima, Sumida-ku (JP); Toshio Yajima, Sumida-ku (JP)

(73) Assignee: Lion Akzo Co., Ltd., Yokkaichi-Shi, Mie (JP)

( * ) Notice: Subject to any disclaimer, the term of this patent is extended or adjusted under 35 U.S.C. 154(b) by 157 days.

(21) Appl. No.: 10/574,561

(22) PCT Filed: Oct. 6, 2004

(86) PCT No.: PCT/JP2004/014717

§ 371 (c)(1),
(2), (4) Date: Apr. 4, 2006

(87) PCT Pub. No.: WO2005/033062

PCT Pub. Date: Apr. 14, 2005

(65) Prior Publication Data

US 2007/0060762 A1     Mar. 15, 2007

(30) Foreign Application Priority Data

Oct. 6, 2003     (JP)     ............... 2003-347145

(51) Int. Cl.
    *C07C 231/00* (2006.01)
(52) U.S. Cl. ..................................... 554/51
(58) Field of Classification Search ............. 554/51
    See application file for complete search history.

(56) References Cited

U.S. PATENT DOCUMENTS 5,470,992 A * 11/1995 Gruning et al. ............... 554/69

FOREIGN PATENT DOCUMENTS

| JP | 08-253446 A | 10/1996 |
| JP | 09-012521 A | 1/1997 |
| JP | 09-235260 A | 9/1997 |
| JP | 11-152260 | * 6/1999 |
| JP | 11-152260 A | 6/1999 |
| JP | 2003-119497 A | 4/2003 |

OTHER PUBLICATIONS

Chem. Abstr. CS-237747, 1985.*

* cited by examiner

*Primary Examiner*—Deborah D Carr
(74) *Attorney, Agent, or Firm*—Buchanan Ingersoll & Rooney PC

(57) ABSTRACT

A production process for a carboxylic amide compound in which color tone stability after the passage of time is good and in order to provide production processes for betaine, a quaternary ammonium salt and an amine salt using the above carboxylic amide compound, a production process for carboxylic amide and derivatives thereof characterized by reacting higher fatty acid or an ester thereof represented by the following Formula (1) with diamine represented by the following Formula (2) under the presence of an organic phosphonic acid compound represented by the following Formula (3) or adding the organic phosphonic acid compound after the reaction or after removing excess diamine after the reaction:

$$R^1\text{—COOR}^2 \quad (1)$$

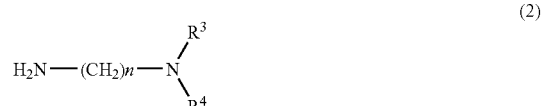

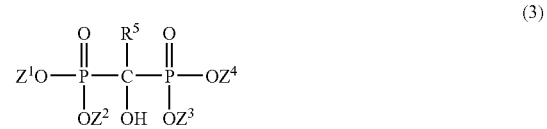

wherein each of the R and Z groups and n are defined.

8 Claims, No Drawings

PRODUCTION PROCESS FOR CARBOXYLIC AMIDE AND DERIVATIVES THEREOF

TECHNICAL FIELD

The present invention relates to a production process for carboxylic amide and derivatives thereof (carboxylic amide compounds) in which a color tone stability after the passage of time is good and a production process for betaine, quaternary ammonium salts and amine salt derivatives using the above carboxylic amide compounds.

BACKGROUND ART

In general, carboxylic amide compounds are known as useful intermediates for cationic surfactants of quaternary ammonium salts and amphoteric surfactants of a betaine type. Also, carboxylic amide itself is used for hair rinses, hair conditioners and the like as an amine salt.

Qualities required to such carboxylic amides and derivatives thereof such as quaternary ammonium salts, betaine and amine salts include a good color tone and a good odor.

Usually, the above carboxylic amide compounds can be produced by subjecting fatty acids or esters thereof and diamine to dehydration and condensation. In general, this condensation reaction proceeds by reacting higher fatty acids or esters thereof with diamine at a reaction temperature of 80 to 200° C. under atmospheric pressure or reduced pressure. Usually, a small amount of impurities present in the raw materials is converted to colored substances by heat or in the presence of a trace amount of air to cause a marked degradation in the color and the odor, and a large effect is exerted on a color tone and an odor of the products and a color tone and an odor of the finished products.

In general, carboxylic amide having a long chain alkyl group has a high melting point and is solid at room temperature, and therefore it is stored in a liquid state under heating or it is stored in the form of a solid matter and has to be molten by heating before producing derivatives such as quaternary ammonium salts and betaine.

However, carboxylic amide causes a deterioration in a color tone by being subjected to heat history to result in exerting an adverse effect on the qualities of the products such as quaternary ammonium salts and betaine.

An improvement in a color tone by adding (10 to 1000 ppm), for example, VIII group metal compounds such as sodium boron hydride ($NaBH_4$) has so far been known as a method for improving a color tone of carboxylic amide and derivatives thereof (refer to, for example, patent documents 1 and 2).

However, in the methods described in these documents, the color tone is not sufficiently improved by a lower limit value (10 ppm) prescribed in the claims, and when the addition amount is increased to 100 ppm or more, the compounds are not dissolved in carboxylic amide to generate precipitates. Further, when the compounds are added in an amount of 1000 ppm and the products are stored under heating, the problem that the base material is decomposed is brought about.

Also, sodium borohydride is a water-prohibiting substance and has the problem that it is difficult to handle in terms of safety since it generates hydrogen in treating.

Patent document 1: Japanese Patent Application Laid-Open No. 253446/1996 (claims, page 3 to page 4 and the like)

Patent document 2: Japanese Patent Application Laid-Open No. 235260/1997 (claims, page 3, examples and the like)

DISCLOSURE OF INVENTION

In light of the problems of the conventional techniques described above, the present invention intends to solve them, and an object thereof is to provide a process for producing carboxylic amide and derivatives thereof in which a color tone and an odor are good by reacting fatty acid or an ester thereof with diamine and a process for producing betaine, quaternary ammonium salts and amine salts in which a color tone and an odor are good by using the above carboxylic amide compounds.

In order to solve the conventional problems described above, the present inventors have intensively investigated a process for producing efficiently carboxylic amide, a quaternary ammonium salt and betaine in which a color tone and an odor are good and which have a high quality by simple operation, and as a result thereof, they have found that a carboxylic amide compound which meets the object described above and in which a color tone and an odor are good can be produced by carrying out reaction under the presence of a specific compound in reacting fatty acid or an ester thereof with diamine and that quaternary ammonium salts, betaine and amine salts in which a color tone and an odor are very good can be produced by reacting the above carboxylic amide compound with a quaternization agent such as alkylhalide, monohaloalkylcarboxylic acid or a salt thereof, or organic acid and/or inorganic acid. Thus, they have come to complete the present invention.

That is, the present invention comprises the following items (1) to (5).

(1) A production process for carboxylic amide and derivatives thereof, characterized by reacting higher fatty acid or an ester thereof represented by the following Formula (1) with diamine represented by the following Formula (2) under the presence of 0.001 to 0.1 mass % of an organic phosphonic acid compound based on the whole amount of the higher fatty acid or the ester thereof described above:

$$R^1\text{—}COOR^2 \tag{1}$$

in Formula (1) described above, $R^1$ represents a linear or branched alkyl group, an alkenyl group or a hydroxyalkyl group having 5 to 23 carbon atoms, and $R^2$ represents a hydrogen atom, a linear or branched alkyl group having 1 to 4 carbon atoms or a residue obtained by removing one acyloxy group from glyceride;

$$H_2N\text{—}(CH_2)_n\text{—}N\begin{smallmatrix}R^3\\ \\R^4\end{smallmatrix} \tag{2}$$

in Formula (2) described above, $R^3$ and $R^4$ represent an alkyl group having 1 to 4 carbon atoms and may be the same or different, and n represents a number of 2 to 4.

(2) A production process for carboxylic amide and derivatives thereof, characterized by reacting higher fatty acid or an ester thereof represented by the following Formula (1) with diamine represented by the following Formula (2) or removing excess diamine after the reaction and then adding 0.001 to 0.1 mass % of an organic phosphonic acid compound based on the whole amount of the higher fatty acid or the ester thereof described above:

$$R^1\text{—}COOR^2 \tag{1}$$

in Formula (1) described above, $R^1$ represents a linear or branched alkyl group, an alkenyl group or a hydroxyalkyl group having 5 to 23 carbon atoms, and $R^2$ represents a hydrogen atom, a linear or branched alkyl group having 1 to 4 carbon atoms or a residue obtained by removing one acyloxy group from glyceride;

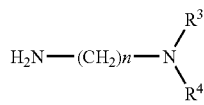

(2)

in Formula (2) described above, $R^3$ and $R^4$ represent an alkyl group having 1 to 4 carbon atoms and may be the same or different, and n represents a number of 2 to 4.

(3) The production process for carboxylic amide and derivatives thereof as described in the above item (1) or (2), wherein the organic phosphonic acid compound is diphosphonic acid or a salt thereof having a structure represented by the following Formula (3):

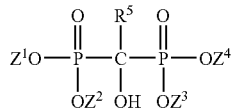

(3)

in Formula (3) described above, $R^5$ represents a hydrogen atom or a lower alkyl group having 1 to 3 carbon atoms, and $Z^1$, $Z^2$, $Z^3$ and $Z^4$ each represent independently a hydrogen atom or an alkaline metal atom.

(4) A production process for betaine, characterized by producing betaine represented by the following Formula (5) by reacting the carboxylic amide compound obtained by the production process as described in the above item (1) to (3) with monohaloalkylcarboxylic acid or a salt thereof represented by the following Formula (4):

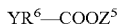 (4)

in Formula (4) described above, Y represents a halogen atom; $R^6$ represents a linear or branched alkylene group having 1 to 3 carbon atoms; and $Z^5$ represents a hydrogen atom or an alkaline metal atom;

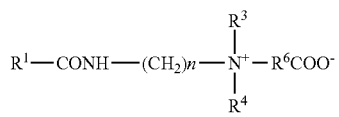

(5)

in Formula (5) described above, $R^1$, $R^3$, $R^4$, $R^6$ and n are the same as described above.

(5) A production process for a quaternary ammonium salt, characterized by producing a quaternary ammonium salt represented by the following Formula (8) by reacting the carboxylic amide compound obtained by the production process as described in the above item (1) to (3) with halogenated alkyl represented by the following Formula (6) or dialkylsulfate represented by the following Formula (7):

(6)

in Formula (6) described above, Y represents a halogen atom, and $R^7$ represents an alkyl group having 1 to 4 carbon atoms;

(7)

in Formula (7) described above, $R^8$ represents an alkyl group having 1 to 4 carbon atoms;

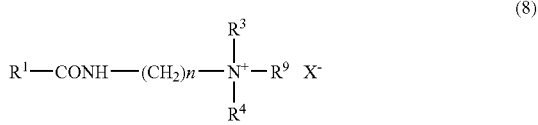

(8)

in Formula (8) described above, $R^1$, $R^3$, $R^4$ and n represent the same meanings as described above; $R^9$ represents $R^7$ or $R^3$; and X represents Y or $R^8SO_4$.

(6) A production process for an amine salt, characterized by producing an amine salt represented by the following Formula (9) by neutralizing the carboxylic amide compound obtained by the production process as described in any of the above items (1) to (3) with at least one neutralizing agent selected from organic acids, inorganic acids and acidic amino acids:

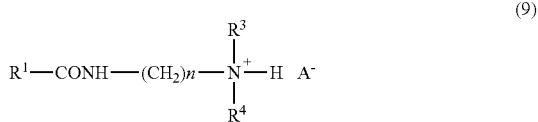

(9)

in Formula (9) described above, $R^1$, $R^3$, $R^4$ and n represent the same meanings as described above, and A represents organic acid, inorganic acid or acidic amino acid.

In the present invention, provided is a production process for carboxylic amide and derivatives thereof in which a color tone and an odor are good and which are excellent in a long term storage stability. Further, betaine, quaternary ammonium salts and amine salts which are produced using the above carboxylic amide are excellent as well in a color tone and an odor, and they are very useful as cosmetic base materials for shampoos, rinses and the like.

BEST MODE FOR CARRYING OUT THE INVENTION

The embodiment of the present invention shall be explained below in details by invention.

The production process for carboxylic amide and derivatives thereof according to present invention (hereinafter referred to as "the first present invention") is characterized by reacting higher fatty acid or an ester thereof represented by the following Formula (1) with diamine represented by the following Formula (2) under the presence of 0.001 to 0.1 mass % of an organic phosphonic acid compound based on the whole amount of the higher fatty acid or the ester thereof described above or adding 0.001 to 0.1 mass % of the organic phosphonic acid compound based on the whole amount of the higher fatty acid or the ester thereof described above after reacting the higher fatty acid or the ester thereof represented by the following Formula (1) with the diamine represented by the following Formula (2) or after removing excess diamine after the reaction:

$$R^1\text{—COOR}^2 \quad (1)$$

in Formula (1) described above, $R^1$ represents a linear or branched alkyl group, an alkenyl group or a hydroxyalkyl group having 5 to 23 carbon atoms, and $R^2$ represents a hydrogen atom, a linear or branched alkyl group having 1 to 4 carbon atoms or a residue obtained by removing one acyloxy group from glyceride;

$$H_2N\text{—}(CH_2)_n\text{—}N\begin{matrix}R^3\\ \\R^4\end{matrix} \quad (2)$$

in Formula (2) described above, $R^3$ and $R^4$ represent an alkyl group having 1 to 4 carbon atoms and may be the same or different, and n represents a number of 2 to 4.

The carboxylic amide and the derivatives thereof used in the first present invention shall not specifically be restricted as long as they are represented by Formula (1). To be specific, they include vegetable oil or animal oil fatty acids such as caprylic acid, capric acid, lauric acid, myristic acid, palmitic acid, stearic acid, oleic acid, behenic acid, erucic acid, 12-hydroxystearic acid, coconut oil fatty acid, cotton seed oil fatty acid, corn oil fatty acid, beef tallow fatty acid, babassu oil fatty acid, palm kernel oil fatty acid, soybean oil fatty acid, flaxseed oil fatty acid, castor oil fatty acid, olive oil fatty acid and whale oil fatty acid, or methyl esters, ethyl esters and glycerides thereof and mixtures thereof. They can be used alone (one kind) or in a mixture of two or more kinds thereof.

Among them, higher fatty acids or lower alkyl esters thereof in which $R^2$ is a hydrogen atom or an alkyl group having 1 to 4 carbon atoms are preferred from the viewpoint of an excellent handling property, and those in which $R^1$ is a linear alkyl group having 9 to 21 carbon atoms and in which $R^2$ is a hydrogen atom or methyl are particularly preferred.

The diamine used in the first present invention shall not specifically be restricted as long as it is represented by Formula (2) described above. To be specific, it includes dimethylaminopropylamine, dimethylaminoethylamine, diethylaminopropylamine, diethylaminoethylamine, dibutylaminopropylamine, dibutylaminoethylamine, dipropylaminopropylamine and dipropylaminoethylamine. They can be used alone (one kind) or in a mixture of two or more kinds thereof.

Among them, dimethylaminopropylamine and diethylaminoethylamine are preferred from the viewpoint of easiness in obtaining the raw materials.

In the first present invention, the organic phosphonic acid compound is added in reacting the higher fatty acid or the ester thereof represented by Formula (1) with the diamine represented by Formula (2) or after the reaction or after removing excess diamine after the reaction.

The carboxylic amide and the derivatives thereof (carboxylic amide compounds) in which a color tone and an odor are good and which are excellent in a long term storage stability can be obtained by using the above organic phosphonic acid compound.

The organic phosphonic acid compound which can be used shall not specifically be restricted, and diphosphonic acid or a salt thereof having a structure represented by the following Formula (3) is preferably used since it does not generate gas such as hydrogen in treating and is easy to handle from an industrial point of view:

$$Z^1O\text{—}\underset{\underset{OZ^2}{\vert}}{\overset{\overset{O}{\|}}{P}}\text{—}\underset{\underset{OH}{\vert}}{\overset{\overset{R^5}{\vert}}{C}}\text{—}\underset{\underset{OZ^3}{\vert}}{\overset{\overset{O}{\|}}{P}}\text{—}OZ^4 \quad (3)$$

in Formula (3) described above, $R^5$ represents a hydrogen atom or a lower alkyl group having 1 to 3 carbon atoms, and $Z^1$, $Z^2$, $Z^3$ and $Z^4$ each represent independently a hydrogen atom or an alkaline metal atom.

The diphosphonic acid or the salt thereof represented by Formula (3) includes, to be specific, hydroxyethanediphosphonic acid, hydroxypropanediphosphonic acid, hydroxybutanediphosphonic acid and salts thereof. Hydroxyethanediphosphonic acid or salts thereof are more preferred from the viewpoint that they are water-soluble and excellent in a handling property.

In respect to timing in which the above organic phosphonic acid compounds are added, they may be added before amidation reaction of the carboxylic amide compound or may be added after the amidation reaction or after removing excess diamine after the amidation reaction. A method in which they are added before the amidation reaction is preferred from the viewpoint of an effect of inhibiting a deterioration in the color tone.

A use amount of the above organic phosphonic acid compound (organic phosphonic acids and/or salts thereof) is 0.001 to 1 mass % (hereinafter "mass %" shall be referred to merely as "%"), preferably 0.003 to 0.1% and more preferably 0.005 to 0.01% based on the whole amount of the higher fatty acid or the ester thereof (fatty acid derivative) each described above.

If a use amount of the above organic phosphonic acid compound is less than 0.001%, the carboxylic amide compound and the derivatives thereof in which stability in a color tone and an odor is satisfactory can not be obtained. On the other hand, if this amount is added in excess over 1.0%, the carboxylic amide compound and the derivatives thereof in which a color tone and an odor are good are obtained, but the organic phosphonic acid compound is present in excess in the composition, and therefore it is disadvantageous in terms of the cost and might cause precipitation.

In the first present invention, a reaction temperature of the higher fatty acid or the ester thereof described above with the diamine described above falls in a range of 80 to 220° C., preferably 90 to 200° C., and the reaction time is 3 to 20 hours, preferably 5 to 10 hours.

A mole ratio of the diamine to the higher fatty acid or the ester thereof described above is usually 1.0 to 2.0, preferably 1.05 to 1.5.

When the fatty acid ester is used, the reaction time can be shortened by carrying out the reaction in the presence of an alkali catalyst such as sodium methoxide. After the reaction, unreacted diamine is preferably distilled off under reduced pressure or by nitrogen blow.

Further, the carboxylic amide compound may be stored at room temperature in the form of a solid matter or may be stored in the form of a liquid under heating. In this case, sealing with nitrogen is preferred from the viewpoint of exhibiting further storage stability. Capable of being given as sealing with nitrogen (including examples described later) are, for example, allowing nitrogen to flow into a head space of a storing vessel, bubbling of nitrogen in the case of a liquid and setting the pressure back to atmospheric pressure by nitrogen after reducing the pressure.

In the first present invention, the carboxylic amide and the derivatives thereof in which a color tone and an odor are good and which are excellent in a long term storage stability are obtained by reacting the higher fatty acid or the ester thereof represented by Formula (1) described above with the diamine represented by Formula (2) described above under the presence of 0.001 to 0.1 mass % of an organic phosphonic acid compound based on the whole amount of the higher fatty acid or the ester thereof described above or adding 0.001 to 0.1 mass % of the organic phosphonic acid compound based on the whole amount of the higher fatty acid or the ester thereof described above after reacting the higher fatty acid or the ester thereof represented by Formula (1) described above with the diamine represented by Formula (2) described above or after removing excess diamine after the reaction.

The specific examples of the carboxylic amide compound obtained in the first present invention include decanoic dimethylaminopropylamide, lauric dimethylaminopropylamide, myristic dimethylaminopropylamide, palmitic dimethylaminopropylamide, stearic dimethylaminopropylamide, coconut oil fatty acid dimethylaminopropylamide, hardened tallow dimethylaminopropylamide, stearic diethylaminoethylamide, isostearic diethylaminoethylamide, oleic diethylaminoethylamide, stearic diethylaminopropylamide, stearic dibutylaminoethylamide, stearic dibutylaminopropylamide, stearic dipropylaminopropylamide, stearic dipropylaminoethylamide, stearic dimethylaminoethylamide, palmitic diethylaminoethylamide, palmitic diethylaminopropylamide, palmitic dimethylaminoethylamide, behenic diethylaminoethylamide, behenic diethylaminopropylamide and behenic dimethylaminopropylamide.

Next, in the production process for betaine according to the present invention (hereinafter referred to as "the second present invention"), betaine represented by the following Formula (5) in which a color tone is markedly good can be obtained by reacting the carboxylic amide compound obtained by the production process described above (the first present invention) with monohaloalkylcarboxylic acid or a salt thereof represented by the following Formula (4):

YR$^6$—COOZ$^5$ (4)

in Formula (4) described above, Y represents a halogen atom; R$^6$ represents a linear or branched alkylene group having 1 to 3 carbon atoms; and Z$^5$ represents a hydrogen atom or an alkaline metal atom;

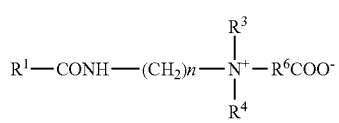

(5)

in Formula (5) described above, R$^1$, R$^3$, R$^4$, R$^6$ and n are the same as described above.

In the second present invention, the carboxylic amide compound can be reacted with the monohaloalkylcarboxylic acid or the salt thereof described above by a method which has so far been publicly known. For example, the carboxylic amide compound is preferably reacted with the monohaloalkylcarboxylic acid or the salt thereof described above by maintaining the pH at 8 to 10 until conversion to betaine is finished and then maintaining the pH in a range of 11.5 to 13 in order to accelerate hydrolysis of remaining monohaloalkylcarboxylic acid salt. The reaction temperature falls more preferably in a range of 50 to 100° C. The reaction may be carried out at normal pressure or under applied pressure.

The monohaloalkylcarboxylic acid or the salt thereof described above which can be used includes, for example, monochloroacetic acid, monobromoacetic acid, monochloropropionic acid, monobromopropionic acid or sodium salts and potassium salts thereof, and monochloroacetic acid or salts thereof are particularly preferred from the viewpoint of easiness in obtaining the raw materials and the handling property.

An amount of the monohaloalkylcarboxylic acid or the salt thereof based on the carboxylic amide compound is preferably 1 to 3 mole ratio, more preferably 1 to 1.15 mole ratio.

If a mole ratio of the above monohaloalkylcarboxylic acid or the salt thereof is less than 1, the unreacted carboxylic amide compound remains. On the other hand, if it exceeds 1.15, an excess amount of the monohaloalkylcarboxylic acid or the salt thereof or the decomposition products thereof remain. Accordingly, both are not preferred.

In the second present invention, the organic phosphonic acid compound or the salt thereof represented by Formula (3) described above is allowed to be preferably present in a range of the addition amount described above in reacting the carboxylic amide compound with the monohaloalkylcarboxylic acid or the salt thereof represented by Formula (4) described above. The betaine in which a color tone is further better can be obtained by allowing the organic phosphonic acid compound or the salt thereof to be present.

In the production process for a quaternary ammonium salt according to the present invention (hereinafter referred to as "the third present invention"), a quaternary ammonium salt represented by the following Formula (8) in which a hue is markedly good is obtained by reacting the carboxylic amide compound obtained by the production process described above with alkylhalide represented by the following Formula (6) or dialkylsulfate represented by the following Formula (7):

YR$^7$ (6)

in Formula (6) described above, Y represents a halogen atom; and R$^7$ represents an alkyl group having 1 to 4 carbon atoms;

R$^8$R$^8$SO$_4$ (7)

in Formula (7) described above, R$^8$ represents an alkyl group having 1 to 4 carbon atoms;

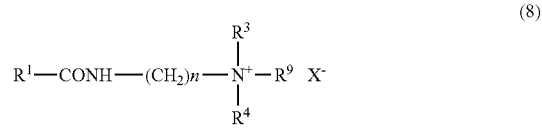

(8)

in Formula (8), R$^1$, R$^3$, R$^4$ and n represent the same meanings as described above; R$^9$ represents R$^7$ or R$^8$; and X represents Y or R$^8$SO$_4$.

In the third present invention, quaternization reaction of the carboxylic amide compound described above with the quaternization agent represented by Formula (6) or Formula (7) each described above, for example, lower alkyl halide such as methyl chloride and dialkylsulfate such as dimethylsulfate can be carried out by a publicly known method.

An amount of the above quaternization agents is preferably 0.95 to 1.5 equivalent, more preferably 0.98 to 1.3 equivalent based on the carboxylic amide compound. If an amount of the above quaternization agents is less than 0.95 equivalent, the reaction time is extended, and a deterioration in the color tone and the odor caused by heat history is liable to be brought about. On the other hand, if it exceeds 1.5 equivalent, the surplus quaternization agent accelerates a deterioration in the color tone and the odor, and the quaternary ammonium salt having a high quality is less liable to be obtained. Further, it is disadvantageous in terms of the cost.

A temperature of the quaternization reaction is higher than a melting point of the carboxylic amide or a mixture of the carboxylic amide and the reaction solvent, and it is preferably 65 to 120° C., more preferably 70 to 100° C. and further preferably 80 to 90° C. in terms of the quality.

Further, in the production process for an amine salt according to the present invention (hereinafter referred to as "the fourth present invention"), an amine salt represented by the following Formula (9) in which a color tone is good can be obtained by neutralizing the carboxylic amide compound obtained by the production process described above with at least one neutralizing agent selected from organic acids, inorganic acids and acidic amino acids:

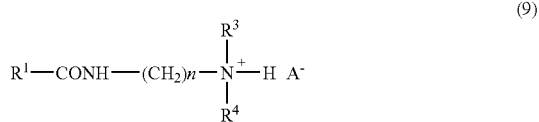

(9)

in Formula (9), $R^1$, $R^3$, $R^4$ and n represent the same meanings as described above, and A represents organic acid, inorganic acid or acidic amino acid.

The neutralizing agent which can be used includes at least one selected from organic acids, inorganic acids and acidic amino acids, and it includes, to be specific, lactic acid, glycolic acid, citric acid, succinic acid, malic acid, hydrochloric acid, sulfulic acid, p-toluenesulfonic acid, phosphoric acid, boric acid, glutamic acid and aspartic acid. Among them, lactic acid and succinic acid are particularly suitably used from the viewpoint that they are not corrosive and used as a raw material for cosmetics. The above neutralizing agents can optionally be used alone or in combination of two or more kinds thereof.

An amount of the neutralizing agent in the present invention is 0.5 to 1.5 equivalent, preferably 0.6 to 1.4 equivalent based on the carboxylic amide compound. If an amount of the above neutralizing agent is less than 0.5 equivalent, the neutralizing reaction is incomplete. On the other hand, if it exceeds 1.4 equivalent, the excess neutralizing agent remains. Accordingly, both are not preferred.

In the fourth present invention, the carboxylic amide compound can be neutralized by a method which has so far been publicly known. For example, the carboxylic amide compound is mixed with the neutralizing agent dissolved in water, and then water is distilled off, whereby the amine salt is obtained. Also, the amine salt is obtained as well by dissolving or dispersing the carboxylic amide compound in warm water and then neutralizing it by adding the neutralizing agent.

Further, a solvent such as ethanol and 2-propanol is added in neutralization, whereby a dissolving amount of the carboxylic amide compound can be raised. The neutralizing temperature is preferably not lower than a melting point of the carboxylic amide compound, and in general, it is 40 to 90° C.

As described above, the carboxylic amide and the derivatives thereof in which a color tone and an odor are good and which are excellent in a long term storage stability are obtained in the first present invention. Further, the betaine, the quaternary ammonium salt and the amine salt in which a color tone and an odor are excellent are obtained in the second present invention to the fourth present invention in which the carboxylic amide compound obtained above is used.

The respective compounds (carboxylic amide compound, betaine, quaternary ammonium salt and amine salt) obtained in the first present invention to the fourth present invention can suitably be used as cleaning agents such as detergents for cloths, detergents for kitchens, shampoos, body shampoos and face washing agents, hair treating agents such as hair rinses, conditioners, treatments and styling foams and fiber treating agents such as softening agents for cloths. Further, optional components can be added to the respective compounds according to the use purposes.

When the respective compounds prepared in the present invention (the first present invention to the fourth present invention) are used, for example, as the hair treating agents, the carboxylic amide of the first present invention, the carboxylic amide salt of the fourth present invention and the quaternary salt of the second present invention are suitably used, and various adding components (optional components) which have so far been used for hair treating agents can be blended if necessary. The above adding components include, for example, anionic surfactants, cationic surfactants, nonionic surfactants, amphoteric surfactants, high polymerization silicon compounds, organic acids such as succinic acid and malic acid or salts thereof, amino acids such as glycine and alanine, anionic polymers, cationic polymers, amphoteric polymers, nonionic polymers, fungicides, higher alcohols, hydrocarbons, natural oils & fats, ester oils, antioxidants, sequestering agents, coloring materials, fragrances, solvents (for example, ethanol, carbitol derivatives and the like), polyhydric alcohols and fatty acids. The above adding components may be added alone or in combination of two or more kinds thereof, and they may be blended in a suitable stage in preparing the hair treating agents.

When the respective compounds prepared in the present invention are used as the cleaning agents, the betaine of the second present invention and the carboxylic amide of the first present invention are suitably used, and various adding components (optional components) which have so far been used for cleaning agents can be blended if necessary. The above adding components include, for example, anionic surfactants, nonionic surfactants, amphoteric surfactants, highly polymerized silicon compounds, organic acids such as succinic acid and malic acid or salts thereof, amino acids such as glycine and alanine, anionic polymers, cationic polymers, amphoteric polymers, nonionic polymers, fungicides, higher alcohols, hydrocarbons, natural oils & fats, ester oils, antioxidants, sequestering agents, coloring materials, fragrances, solvents (for example, ethanol, carbitol derivatives and the like), polyhydric alcohols and fatty acids. The above adding components may be added alone or in combination of two or more kinds thereof.

EXAMPLES

Next, the present invention shall be explained in further detail with reference to examples and comparative examples, but the present invention shall not be restricted to the examples described below.

Example 1

A four neck flask of one liter equipped with a stirrer, a thermometer and a reflux condenser was charged with 350 g of stearic acid (1.23 mole, NAA 173K, molecular weight: 285, manufactured by Nihon Oil & Fat Corporation) and 0.058 g of a hydroxyethanediphosphonic acid 60% aqueous solution (0.01% based on stearic acid, manufactured by Tokyo Kasei Kogyo Co., Ltd.), and the solution was heated at 80° C. to dissolve stearic acid.

Then, after substitution with nitrogen (reduced pressure 6.7 kPa→set back to atmospheric pressure by nitrogen) was carried out twice, the temperature was elevated up to 185° C., and 151 g of N,N-dimethyl-1,3-diaminopropane (hereinafter abbreviated as DMAPA, molecular weight: 102, manufactured by Tokyo Kasei Kogyo Co., Ltd.) was dropwise added thereto in 4 hours. The solution was maintained at 190 to 200° C. during dropwise adding, and then it was ripened for 5 hours. The acid value was measured to result in confirming that it was 2.1 mg-KOH/g and that an amount of unreacted fatty acid was 1.5% or less. Then, the pressure was reduced to 2.0 kPa at 190° C., and topping was carried out for one hour to distil off the unreacted N,N-dimethyl-1,3-diaminopropane.

After topping, the solution was cooled down to 90° C., and then the reaction mixture was taken out. An amine value of this reaction mixture was measured by means of a titrator to result in finding that it was 152 mg-KOH/g. Further, the color tone was measured by means of a color difference analyzer (OME-200, manufactured by Nippon Denshoku Industries Co., Ltd.) to result in finding that the color tone was APHA 100.

Example 2

The same four neck flask of one liter equipped with a stirrer, a thermometer and a reflux condenser as in Example 1 described above was charged with 256.5 g of palmitic acid (1.0 mole, NAA 160, molecular weight: 256.5, manufactured by Nihon Oil & Fat Corporation), and it was heated at 80° C. to melt palmitic acid. Then, after substitution with nitrogen (reduced pressure 6.7 kPa→set back to atmospheric pressure by nitrogen) was carried out twice, the temperature was elevated up to 185° C., and 139 g of N,N-diethylaminoethylamine (hereinafter abbreviated as DEAEA, molecular weight: 116, manufactured by Tokyo Kasei Kogyo Co., Ltd.) was dropwise added thereto in 4 hours. The liquid was maintained at 190 to 200° C. during dropwise adding, and then it was ripened for 8 hours. The acid value was measured to result in confirming that it was 3 mg-KOH/g and that an amount of the unreacted fatty acid was 1.5% or less. Then, the pressure was reduced to 2.0 kPa at 190° C., and topping was carried out for one hour to distil off unreacted N,N-diethylaminoethylamine.

After topping, the solution was cooled down to 110° C., and 0.021 g of a hydroxyethanediphosphonic acid 60% aqueous solution (0.005% based on palmitic acid) was added and mixed. Then, the reaction mixture was taken out, and an amine value of the reaction mixture was measured by means of the titrator to result in finding that it was 144 mg-KOH/g. Further, the color tone was measured by means of the color difference analyzer to result in finding that the color tone was APHA 120.

Example 3

The same four neck flask of one liter equipped with a stirrer, a thermometer and a reflux condenser as in Example 1 described above was charged with 350 g of methyl laurate (1.64 mole, Pastel M12, molecular weight: 214, manufactured by Lion Oleochemical Co., Ltd.) and 0.29 g of a hydroxyethanediphosphonic acid 60% aqueous solution (0.05% based on methyl laurate, manufactured by Tokyo Kasei Kogyo Co., Ltd.), and the solution was heated at 80° C. After substitution with nitrogen (reduced pressure 6.7 kPa→set back to atmospheric pressure by nitrogen) was carried out twice, the temperature was elevated up to 185° C., and 201 g of N,N-dimethyl-1,3-diaminopropane (molecular weight: 102, manufactured by Tokyo Kasei Kogyo Co., Ltd.) was dropwise added thereto in 4 hours. The solution was maintained at 190 to 200° C. during dropwise adding, and then it was ripened for 8 hours. An amount of the unreacted methyl ester was measured by means of gas chromatography to result in finding that it was 0.3%. Then, the pressure was reduced to 2.0 kPa at 190° C., and topping was carried out for one hour to distil off unreacted N,N-dimethyl-1,3-diaminopropane.

After topping, the solution was cooled down to 90° C., and then the reaction mixture was taken out. An amine value of this reaction mixture was measured by means of the titrator to result in finding that it was 193 mg-KOH/g. Further, the color tone was measured by means of the color difference analyzer to result in finding that the color tone was APHA 30.

Comparative Example 1

Reaction was carried out on the same conditions as in Example 1 described above, except that hydroxyethanediphosphonic acid was not used. The acid value was measured to result in confirming that it was 2.2 mg-KOH/g and that an amount of the unreacted fatty acid was 1.5% or less. Then, the pressure was reduced to 2.0 kPa at 190° C., and topping was carried out for one hour to distil off unreacted N,N-dimethyl-1,3-diaminopropane.

After topping, the solution was cooled down to 90° C., and then the reaction mixture was taken out. An amine value of this reaction mixture was measured by means of the titrator to result in finding that it was 152 mg-KOH/g. Further, the color tone was measured by means of the color difference analyzer to result in finding that the color tone was APHA 250.

Comparative Example 2

Reaction was carried out on the same conditions as in Example 3 described above, except that hydroxyethanediphosphonic acid was not used. An amount of the unreacted methyl ester was measured by means of gas chromatography to find that it was 0.3%. Then, the pressure was reduced to 2.0 kPa at 190° C., and topping was carried out for one hour to distil off unreacted N,N-dimethyl-1,3-diaminopropane.

After topping, the solution was cooled down to 90° C., and then the reaction mixture was taken out. An amine value of this reaction mixture was measured by means of the titrator to result in finding that it was 193 mg-KOH/g. Further, the color tone was measured by means of the color difference analyzer to result in finding that the color tone was APHA 150.

Example 4

The same four neck flask of one liter equipped with a stirrer, a thermometer and a reflux condenser as in Example 1 described above was charged with 350 g of methyl stearate (1.17 mole, Pastel M180, molecular weight: 299, manufactured by Lion Oleochemical Co., Ltd.) and 0.058 g of a hydroxyethanediphosphonic acid 60% aqueous solution (0.01% based on methyl stearate, manufactured by Tokyo Kasei Kogyo Co., Ltd.), and the solution was heated at 80 to 100° C. After substitution with nitrogen (reduced pressure 6.7 kPa set back to atmospheric pressure by nitrogen) was carried out twice, the temperature was elevated up to 185° C., and 144 g of N,N-dimethyl-1,3-diaminopropane (molecular weight: 102, manufactured by Tokyo Kasei Kogyo Co., Ltd.) was dropwise added thereto in 4 hours. The solution was maintained at 190 to 200° C. during dropwise adding, and then it was ripened for 8 hours. An amount of the unreacted methyl ester was measured by means of gas chromatography to result in confirming that it was 0.4%. Then, the pressure was reduced to 2.0 kPa at 190° C., and topping was carried out for one hour to distil off unreacted N,N-dimethyl-1,3-diaminopropane.

After topping, the solution was cooled down to 90° C., and then the reaction mixture was taken out. An amine value of this reaction mixture was measured by means of the titrator to result in finding that it was 152 mg-KOH/g. Further, the color tone was measured by means of the color difference analyzer to result in finding that the color tone was APHA 50.

The above carboxylic amide compound was sealed with nitrogen and then subjected to a storage stability test at 100° C. for 7 days. The color tone was measured by means of the color difference analyzer to result in finding that the color tone was Gardner 1 and that the color tone stability was good.

Example 5

Reaction was carried out for 10 hours by the same method as in Example 1 described above, except that lauric acid (molecular weight: 200, manufactured by Acidchem Co., Ltd.) was used in place of stearic acid and that the reaction was carried out in the presence of 0.005% of hydroxyethanediphosphonic acid. The color tone was measured by means of the color difference analyzer to result in finding that the color tone was APHA 100. The above carboxylic amide compound was sealed with nitrogen and then subjected to a storage stability test at 100° C. for 7 days. The color tone was measured by means of the color difference analyzer to result in finding that the color tone was Gardner 1 and that the color tone stability was good.

Example 6

Stearic acid was used to carry out reaction for 10 hours by the same method as in Example 1 described above, except that hydroxyethanediphosphonic acid was added before the reaction, and 0.1% of hydroxyethanediphosphonic acid was added after topping. The color tone was measured by means of the color difference analyzer to result in finding that the color tone was APHA 120. The above carboxylic amide compound was subjected to a storage stability test at 100° C. for one day without sealing with nitrogen. The color tone was measured by means of the color difference analyzer to result in finding that the color tone was Gardner 1.

Comparative Example 3

Reaction was carried out on the same conditions as in Example 4 described above, except that hydroxyethanediphosphonic acid was not added. The above carboxylic amide compound was sealed with nitrogen and then subjected to a storage stability test at 100° C. for 7 days. The color tone was measured by means of the color difference analyzer to result in finding that the color tone was Gardner 4.

Comparative Example 4

Reaction was carried out on the same conditions as in Example 5 described above, except that hydroxyethanediphosphonic acid was not added. The above carboxylic amide compound was sealed with nitrogen and then subjected to a storage stability test at 100° C. for 7 days. The color tone was measured by means of the color difference analyzer to result in finding that the color tone was Gardner 5.

Comparative Example 5

Reaction was carried out on the same conditions as in Example 6 described above, except that hydroxyethanediphosphonic acid was not added. The above carboxylic amide compound was sealed with nitrogen and then subjected to a storage stability test at 100° C. for 7 days. The color tone was measured by means of the color difference analyzer to result in finding that the color tone was Gardner 6.

Example 7

A glass autoclave of one liter was charged with 250 g of carboxylic amide (amine value: 152) synthesized in the same manner as in Example 4 described above, 128 g of stearyl alcohol (manufactured by Kanto Chemical Co., Inc.), 128 g of cetyl alcohol (manufactured by Kanto Chemical Co., Inc.), 18.4 g of ethanol (manufactured by Kanto Chemical Co., Inc.) and 1.4 g of sodium hydrogencarbonate (manufactured by Asahi Glass Co., Ltd.), and they were heated and dissolved wile stirring. Then, substitution with nitrogen (reduced pressure 0.2 kPa→atmospheric pressure) was carried out three times. After reaching 65° C., methyl chloride (manufactured by Sumitomo Seika Chemicals Co., Ltd.) was charged in an amount of 1.03 time mole based on amine, and the solution was ripened at 85 to 100° C. for 2.5 hours. It was confirmed that the total of free amine and amine hydrochloride was 1% or less, and then the reaction was finished. The pressure was removed, and the solution was cooled to room temperature and solidified to obtain a flaky quaternary ammonium salt. The quaternary ammonium salt was dissolved so that the concentration was 50 mass % based on 2-propanol, and then the color tone was measured by means of the color difference analyzer to result in finding that it was APHA 30. Further, an odor of the quaternary ammonium salt was judged by functional evaluation to find that it was good.

Example 8

A four neck flask of 2 liter equipped with a stirrer, a thermometer, a dropping funnel and a cooling tube was charged with 181 g of carboxylic amide synthesized in the same manner as in Example 5 described above, 480 g of ion-exchanged water, 79 g of sodium monochloroacetate (molecular weight: 116.5, manufactured by Kanto Chemical Co., Ltd.) and 6.9 g of a sodium hydroxide aqueous solution (diluted to 30%, manufactured by Kanto Chemical Co., Ltd.), and then the temperature was elevated up to 90° C. Thereafter, the solution was ripened for 5 hours and then cooled down to obtain lauramidepropylbetaine having AI of 30%. A color tone of the above product was measured by means of the color difference analyzer to result in finding that the color tone was APHA 40. Further, an odor of the betaine obtained was judged to find it was good.

Example 9

A four neck flask of one liter was charged with 250 g of carboxylic amide (amine value: 152) synthesized in the same manner as in Example 1 described above, and it was molten at 70 to 80° C. while stirring. Then, a p-toluenesulfonic acid aqueous solution prepared by dissolving 116 g of p-toluenesulfonic acid monohydrate (manufactured by Kanto Chemical Co., Inc.) in 117 g of water was slowly added thereto to neutralize it. Water was distilled off under reduced pressure while maintaining the temperature at 70 to 80° C., and the liquid was cooled to room temperature and solidified to obtain a flaky amine salt. The amine salt was dissolved so that the concentration was 50 mass % based on 2-propanol, and then the color tone was measured by means of the color difference analyzer to result in finding that it was APHA 60. Further, an odor of the amine salt was judged to find that it was good.

Comparative Example 6

A quaternary ammonium salt was synthesized on the same conditions as in Example 6 using 250 g of carboxylic amide synthesized in the same manner as in Comparative Example 3 described above. The quaternary ammonium salt was dissolved so that the concentration was 50 mass % based on 2-propanol, and then the color tone was measured by means of the color difference analyzer to result in finding that the color tone was APHA 150. Further, an odor of the quaternary ammonium salt was judged to find that the odor was strong and inferior.

Comparative Example 7

Betaine was synthesized on the same conditions as in Example 8 using carboxylic amide synthesized in the same manner as in Comparative Example 4 described above. A color tone of the above product was measured by means of the color difference analyzer to result in finding that the color tone was APHA 250. Further, an odor of the betaine obtained was judged to find that the odor was strong and inferior.

Comparative Example 8

An amine salt was synthesized on the same conditions as in Example 9 using carboxylic amide synthesized in the same manner as in Comparative Example 1 described above. The amine salt was dissolved so that the concentration was 50 mass % based on 2-propanol, and then the color tone was measured by means of the color difference analyzer to result in finding that the color tone was APHA 140. Further, an odor of the amine salt was judged to find that the odor was strong and inferior.

The test results of Examples 1 to 3 and Comparative Examples 1 to 2 each described above are shown in the following Table 1; the test results of Examples 4 to 6 and Comparative Examples 3 to 5 each described above are shown in the following Table 2; and the test results of Examples 7 to 9 and Comparative Examples 6 to 8 each described above are shown in the following Table 3.

TABLE 1

| | Fatty acid derivative | Diamine | Additives (addition amount) | Addition timing | Color tone (APHA) |
|---|---|---|---|---|---|
| Example 1 | Stearic acid | DMAPA | Hydroxyethanediphosphonic acid 0.01% | Before reaction | 100 |
| Example 2 | Palmitic acid | DEAEA | Hydroxyethanediphosphonic acid 0.005% | After topping | 120 |
| Example 3 | Methyl laurate | DMAPA | Hydroxyethanediphosphonic acid 0.05% | Before reaction | 30 |
| Comparative Example 1 | Stearic acid | DMAPA | No addition | No addition | 250 |
| Comparative Example 2 | Methyl laurate | DMAPA | No addition | No addition | 150 |

TABLE 2

| | Fatty acid derivative | Diamine | Addition amount of hydroxyethanediphosphonic acid | Storing temperature (° C.) | Storing period (day) | Nitrogen sealing | Color tone (G/H) |
|---|---|---|---|---|---|---|---|
| Example 4 | Methyl stearate | DMAPA | 0.01% | 100 | 7 | Present | 1 |
| Example 5 | Lauric acid | DMAPA | 0.005% | 100 | 7 | Present | 1 |
| Example 6 | Stearic acid | DMAPA | 0.1% | 100 | 1 | None | 1 |
| Comparative Example 3 | Methyl stearate | DMAPA | No addition | 100 | 7 | Present | 4 |
| Comparative Example 4 | Lauric acid | DMAPA | No addition | 100 | 7 | Present | 5 |
| Comparative Example 5 | Stearic acid | DMAPA | No addition | 100 | 1 | None | 6 |

TABLE 3

| | Fatty acid derivative | Diamine | Addition amount of hydroxyethanediphosphonic acid | Derivative | Derivative color tone (APHA) | Derivative odor |
|---|---|---|---|---|---|---|
| Example 7 | Methyl stearate | DMAPA | 0.01% | Quaternary ammonium salt | 30 | ○ |
| Example 8 | Lauric acid | DMAPA | 0.005% | Betaine | 40 | ○ |
| Example 9 | Stearic acid | DMAPA | 0.01% | Amine salt | 60 | ○ |
| Comparative Example 6 | Methyl stearate | DMAPA | No addition | Quaternary amine | 150 | X |
| Comparative Example 7 | Lauric acid | DMAPA | No addition | Betaine | 250 | X |
| Comparative Example 8 | Stearic acid | DMAPA | No addition | Amine salt | 140 | X |

As apparent from the results shown in Table 1 and Table 2 each described above, it has been confirmed that the carboxylic amide compounds in which a color tone is good are obtained in Examples 1 to 6 falling in the scope of the present invention as compared with Comparative Examples 1 to 5 falling outside the scope of the present.

Further, as apparent from the results shown in Table 3 described above, it has been confirmed that the betaines, the quaternary ammonium salts and the amine salts in which a color tone and an odor are good are obtained in Examples 7 to 9 falling in the scope of the present invention as compared with Comparative Examples 6 to 8 falling outside the scope of the present.

INDUSTRIAL APPLICABILITY

The carboxylic amide compounds which are obtained according to the present invention and in which a color tone stability after the passage of time is good are useful as intermediates for cationic surfactants of quaternary ammonium salts and amphoteric surfactants of a betaine type, and the carboxylic amides themselves are suitably used for rinses, conditioners and the like as amine salts.

What is claimed is:

1. A production process for carboxylic amide, characterized by reacting higher fatty acid or an ester thereof represented by the following Formula (1) with diamine represented by the following Formula (2) under the presence of 0.001 to 0.1 mass % of an organic phosphonic acid compound based on the whole amount of the higher fatty acid or the ester thereof described above:

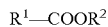
$$R^1\text{—COOR}^2 \tag{1}$$

in Formula (1) described above, $R^1$ represents a linear or branched alkyl group, an alkenyl group or a hydroxyalkyl group having 5 to 23 carbon atoms, and $R^2$ represents a hydrogen atom, a linear or branched alkyl group having 1 to 4 carbon atoms or a residue obtained by removing one acyloxy group from glyceride;

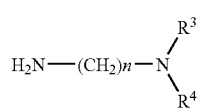

$$H_2N\text{—}(CH_2)n\text{—}N\begin{matrix}R^3\\ \\R^4\end{matrix} \tag{2}$$

in Formula (2) described above, $R^3$ and $R^4$ represent an alkyl group having 1 to 4 carbon atoms and may be the same or different, and n represents a number of 2 to 4.

2. The production process for carboxylic amide as described in claim 1, wherein the organic phosphonic acid compound is diphosphonic acid or a salt thereof having a structure represented by the following Formula (3):

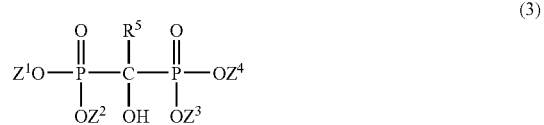

in Formula (3) described above, $R^5$ represents a hydrogen atom or a lower alkyl group having 1 to 3 carbon atoms, and $Z^1$, $Z^2$, $Z^3$ and $Z^4$ each represent independently a hydrogen atom or an alkaline metal atom.

3. A production process for betaine, characterized by producing betaine represented by the following Formula (5) by reacting the carboxylic amide compound obtained by the production process as described in claim 1 with monohaloalkylcarboxylic acid or a salt thereof represented by the following Formula (4):

$$YR^6\text{—}COOZ^5 \tag{4}$$

in Formula (4) described above, Y represents a halogen atom; $R^6$ represents a linear or branched alkylene group having 1 to 3 carbon atoms; and $Z^5$ represents a hydrogen atom or an alkaline metal atom;

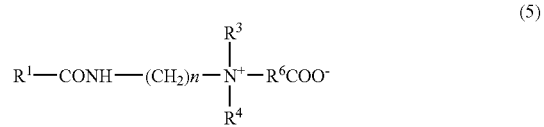

in Formula (5) described above, $R^1$, $R^3$, $R^4$, $R^6$ and n are the same as described above.

4. A production process for betaine, characterized by producing betaine represented by the following Formula (5) by reacting the carboxylic amide compound obtained by the production process as described in claim 2 with monohaloalkylcarboxylic acid or a salt thereof represented by the following Formula (4):

$$YR^6\text{—}COOZ^5 \tag{4}$$

in Formula (4) described above, Y represents a halogen atom; $R^6$ represents a linear or branched alkylene group having 1 to 3 carbon atoms; and $Z^5$ represents a hydrogen atom or an alkaline metal atom;

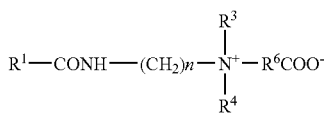

in Formula (5) described above, $R^1$, $R^3$, $R^4$, $R^6$ and n are the same as described above.

5. A production process for a quaternary ammonium salt, characterized by producing a quaternary ammonium salt represented by the following Formula (8) by reacting the carboxylic amide compound obtained by the production process as described in claim 1 with halogenated alkyl represented by the following Formula (6) or dialkylsulfate represented by the following Formula (7):

$$YR^7 \tag{6}$$

in Formula (6) described above, Y represents a halogen atom, and $R^7$ represents an alkyl group having 1 to 4 carbon atoms;

$$R^8R^8SO_4 \tag{7}$$

in Formula (7) described above, $R^8$ represents an alkyl group having 1 to 4 carbon atoms;

in Formula (8) described above, $R^1$, $R^3$, $R^4$ and n represent the same meanings as described above; $R^9$ represents $R^7$ or $R^8$; and X represents Y or $R^8SO_4$.

6. A production process for a quaternary ammonium salt, characterized by producing a quaternary ammonium salt represented by the following Formula (8) by reacting the carboxylic amide compound obtained by the production process as described in claim 2 with halogenated alkyl represented by the following Formula (6) or dialkylsulfate represented by the following Formula (7):

$$YR^7 \tag{6}$$

in Formula (6) described above, Y represents a halogen atom, and $R^7$ represents an alkyl group having 1 to 4 carbon atoms;

$$R^8R^8SO_4 \tag{7}$$

in Formula (7) described above, $R^8$ represents an alkyl group having 1 to 4 carbon atoms;

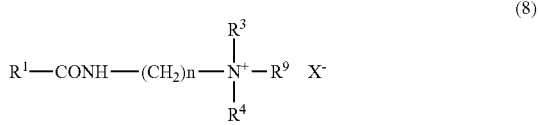

in Formula (8) described above, $R^1$, $R^3$, $R^4$ and n represent the same meanings as described above; $R^9$ represents $R^7$ or $R^8$; and X represents Y or $R^8SO_4$.

7. A production process for an amine salt, characterized by producing an amine salt represented by the following Formula (9) by neutralizing the carboxylic amide compound obtained by the production process as described in claim 1 with at least one neutralizing agent selected from organic acids, inorganic acids and acidic amino acids:

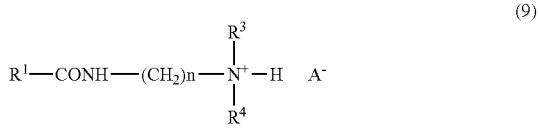

in Formula (9) described above, $R^1$, $R^3$, $R^4$ and n represent the same meanings as described above, and A represents organic acid, inorganic acid or acidic amino acid.

8. A production process for an amine salt, characterized by producing an amine salt represented by the following Formula (9) by neutralizing the carboxylic amide compound obtained by the production process as described in claim 2 with at least one neutralizing agent selected from organic acids, inorganic acids and acidic amino acids:

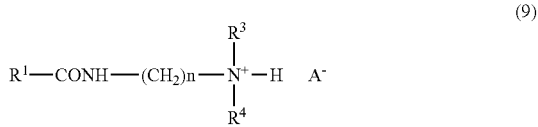

in Formula (9) described above, $R^1$, $R^3$, $R^4$ and n represent the same meanings as described above, and A represents organic acid, inorganic acid or acidic amino acid.

* * * * *